United States Patent
Sarr et al.

(10) Patent No.: US 8,234,942 B2
(45) Date of Patent: Aug. 7, 2012

(54) STRINGER PROBE WITH MAGNETIC SPRING BALANCE

(75) Inventors: Dennis P. Sarr, Kent, WA (US); James C. Kennedy, Renton, WA (US); Hien T. Bui, Renton, WA (US)

(73) Assignee: The Boeing Company, Chicago, IL (US)

( * ) Notice: Subject to any disclaimer, the term of this patent is extended or adjusted under 35 U.S.C. 154(b) by 326 days.

(21) Appl. No.: 12/642,478

(22) Filed: Dec. 18, 2009

(65) Prior Publication Data

US 2011/0146424 A1    Jun. 23, 2011

(51) Int. Cl.
*G01M 19/00* (2006.01)
(52) U.S. Cl. .................................................. 73/865.8
(58) Field of Classification Search .................. None
See application file for complete search history.

(56) References Cited

U.S. PATENT DOCUMENTS

| | | | | |
|---|---|---|---|---|
| 6,722,202 | B1 | 4/2004 | Kennedy et al. | 73/634 |
| 7,228,741 | B2 | 6/2007 | Georgeson et al. | 73/634 |
| 7,231,826 | B2 | 6/2007 | Bossi et al. | 73/618 |
| 7,249,512 | B2 | 7/2007 | Kennedy et al. | 73/618 |
| 7,263,889 | B2 | 9/2007 | Kennedy et al. | 73/620 |
| 7,320,249 | B2 * | 1/2008 | Georgeson et al. | 73/634 |
| 2006/0042391 | A1 | 3/2006 | Georgeson | |
| 2006/0055396 | A1 | 3/2006 | Georgeson | |
| 2006/0055399 | A1 * | 3/2006 | Georgeson et al. | 324/232 |
| 2006/0162456 | A1 | 7/2006 | Kennedy et al. | 73/620 |

OTHER PUBLICATIONS

J.E. Michaels et al., "Self-Calibrating Ultrasonic Methods for In-Situ Monitoring of Fatigue Crack Progression", Review of Quantitative Nondestructive Evaluation, vol. 24, American Inst. Of Physics, 0-7354-0245-0/05 (2005), pp. 1765-1772.
T.E. Michaels, "Application of Acoustic Wavefield Imaging to Non-Contact Ultrasonic Inspection of Bonded Components", Review of Quantitative Nondestructive Evaluation, vol. 25, American Inst. Of Physics, 0-7354-0312-0/06 (2006), pp. 1484-1491.
International Search Report mailed Feb. 21, 2011.

\* cited by examiner

*Primary Examiner* — Robert R Raevis
(74) *Attorney, Agent, or Firm* — Caven & Aghevli LLC

(57) ABSTRACT

A nondestructive inspection apparatus and method for inspecting a structure having an interior opening portion may comprise an inspection apparatus outer probe unit having a plurality of outer probe unit walls each having a surface corresponding to a respective one of the plurality of exterior surfaces of a respective structure wall, the outer probe unit may comprise a first outer probe member and a second outer probe member, magnetically coupled to each other through magnetic attraction between a magnet on the first outer probe unit member and a magnet on the second outer probe unit member; and a magnetic balance positioned to force the second outer probe unit member in a direction of increased magnetic coupling of the second outer probe unit member to the first outer probe unit member through magnetic repulsion between a magnet on the magnetic balance and a magnet on the second outer probe unit member.

15 Claims, 5 Drawing Sheets

STRINGER PROBE WITH MAGNETIC SPRING BALANCE

FIELD OF THE INVENTION

The present disclosure relates generally to an apparatus and method for inspecting a structure, and more particularly, to an apparatus and structure for non-destructive testing of limited-access features of a structure such as stringers.

BACKGROUND

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or flaws in the structure. NDI is also used in the initial fabrication of the aircraft's structural components. It is used to assure there was not a process problem when fabrication of the part or possible foreign material embedded within the part. Inspection may be performed during manufacturing of a structure and/or once a structure is in-service. For example, inspection may be required to validate the integrity and fitness of a structure for continued use in manufacturing and future ongoing use in-service. However, access to interior surfaces is often more difficult or impossible without disassembly, such as removing a part for inspection from an aircraft.

Among the structures that are routinely non-destructively tested are composite structures, such as composite sandwich structures and other adhesive bonded panels and assemblies, such as hat stringers or hat stiffeners made from carbon fiber reinforced and graphite epoxy (Gr/Ep) materials and co-cured or co-bonded hat stringers. In this regard, composite structures are commonly used throughout the aircraft industry because of the engineering qualities, design flexibility and low weight, such as the stiffness-to-weight ratio. As such, it is frequently desirable to inspect composite structures to identify any flaws, such as cracks, voids or porosity, which could adversely affect the performance of the composite structure.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, foreign material detection, and/or crack detection in the structure. Resonance, pulse echo or mechanical impedance sensors may be used to provide indications of voids or porosity, such as in adhesive bondlines of the structure. High resolution inspection of aircraft structure are commonly performed using semi-automated ultrasonic testing (UT) to provide a plan view image of the part or structure under inspection. For example, solid laminates may be inspected using one-sided pulse echo ultrasonic (PEU) testing and composite sandwich structures may be inspected using two-sided through-transmission ultrasonic (TTU) testing. In pulse echo ultrasonic (PEU) testing, ultrasonic sensors, such as ultrasonic transducers, are positioned adjacent to or near one surface of the structure to be inspected. For example, the PEU transducer transmits an ultrasonic signal into the structure under inspection and receives the reflection of the ultrasonic signal from the structure. In through-transmission ultrasonic inspection, paired ultrasonic sensors such as transducers, or transducer and a receiver pairings, are positioned facing the other but contacting opposite sides of the structure. An ultrasonic signal is transmitted by at least one of the transducers, propagated through the structure, and received by the other transducer. Data acquired by sensors, such as PEU and TTU transducers, is typically processed by a processing element, and the processed data may be presented to a user via a display. A data acquisition board and data handling software may be used for collection and display of inspection data, such as displaying the data on a computer monitor as an image representation of the structure under inspection, such as a hat stringer, supplemented with corresponding color and/or graphical data of the inspection to permit examination by a qualified inspector.

Non-destructive inspection may be performed manually by technicians who typically move an appropriate sensor over the structure. Manual scanning requires a trained technician to move the sensor over all portions of the structure needing inspection. Manual scanning typically involves the technician repeatedly moving a sensor side-to-side in one direction while simultaneously indexing the sensor in another direction. In addition, because sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have also been developed. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS [MiniMAUS] systems may be portable units manually moved over the surface of a structure by a technician.

Automated inspection systems have also been developed. For example, the Automated Ultrasonic Scanning System (AUSS®) system is a complex mechanical scanning system that may employ through-transmission ultrasonic inspection. An AUSS system can also perform pulse echo inspections, and simultaneous dual frequency inspections. The AUSS system has robotically controlled probe arms that may be positioned, for example, for TTU inspection proximate the opposed surfaces of the structure undergoing inspection with one probe arm moving an ultrasonic transmitter along one surface of the structure, and the other probe arm correspondingly moving an ultrasonic receiver along the opposed surface of the structure. To maintain the ultrasonic transmitter and receiver in proper alignment and spacing with one another and with the structure undergoing inspection, a conventional automated inspection system may have a complex positioning system that provides motion control in numerous axes, such as the AUSS-X system which has motion control in ten axes. Automated inspection systems, and like robotics, however, can be prohibitively expensive. Further, orienting and spacing sensors with respect to the structure, and with respect to one another for TTU inspection, may be especially difficult in conjunction with structures with non-planar shapes, such as the inspection of curved structures and hat stringers. Also, conventional automated scanning systems, such as the AUSS-X system, may require access to both sides of a structure which, at least in some circumstances, will be problematic, if not impossible, particularly for very large or small structures. Furthermore, scanning systems inspect limited areas up to a few meters square. Accessibility to the structure requiring inspection and to particular features is also an important consideration. Access may be so limited that manual inspection or automated inspection is not possible. For example, the inside of a hat stringer of the fuselage of an aircraft has limited access for inspection, especially far from an end.

The aforesaid background discussion derives from U.S. Pat. Nos. 7,249,512 and 7,263,889. See also U.S. Pat. Nos. 7,231,826 and 6,722,202 in which are described various apparatus and methods for nondestructively inspecting a structure formed having a length of interior space surrounded by, for example, a hat stringer formed as a support member for such as aircraft wings and fuselage bodies. Such nondestructive inspection (NDI) probes have been sensing elements, such as ultrasonic transducers, disposed proximate one or more of the surfaces of a structure, top and bottom or side walls. Often the transducer(s) of such a probe needs to interact with a transducer on the opposite side of the structure wall, and thus an inner transducer holding probe magnetically coupled to an exterior probe assembly outside of the structure, such as a hat stringer, travels with the exterior probe. The magnetic coupling along with hinged or flexible corners on one or both of the probes are known for use to re-orient the position, shape, configuration and/or alignment of one or both of the probes with respect to changes in the hat stringer for various shapes, sizes, and configurations of hat stingers.

Magnetic coupling is very sensitive to distance between opposing magnets on the inner holder probe member and the exterior transducer fixture probe assembly unit. Thus, conventional systems provide for adjustability of the shape of the inner and outer probe assemblies and/or the width of the inner probe to try to keep the probe sidewalls in as close a contact with the respective surfaces of the respective walls of the structure, interior and exterior. Notwithstanding, magnetic decoupling may occur, requiring, e.g., a recoupling and rerunning of the inspection with the interior probe and exterior assembly recoupled magnetically. It is believed that a major contributor to this phenomenon is surface roughness and/or surface irregularities on the structure. The magnetic coupling force between the coupling magnets on the inner probe and exterior transducer fixture assembly drops off very significantly with a relatively small increase in the distance separating the magnets.

SUMMARY

A nondestructive inspection apparatus and method is disclosed for inspecting a structure having an interior opening portion defined by a plurality of walls having exterior and interior surfaces, which may comprise an inspection apparatus outer probe unit having a plurality of outer probe unit walls each having a surface corresponding to a respective one of the plurality of exterior surfaces of a respective structure wall, comprising a first outer probe member and a second outer probe member, magnetically coupled to each other to thereby force at least one outer probe unit wall on the first outer probe unit member and at least one outer probe unit wall on the second outer probe unit member into close proximity to a respective exterior surface of the structure, through magnetic attraction between a magnet on the first outer probe unit member and a magnet on the second outer probe unit member; and a magnetic balance positioned to force the second outer probe unit member in a direction of increased magnetic coupling of the second outer probe unit member to the first outer probe unit member through magnetic repulsion between a magnet on the magnetic balance and a magnet on the second outer probe unit member. The apparatus may further comprise an inspection apparatus inner probe unit having a plurality of inner probe unit walls each having a surface corresponding to a respective one of the interior surfaces of the structure; and the inner probe unit being magnetically coupled through the structure to the outer probe unit by magnetic attraction of a magnet on the inner probe unit and a magnet on the outer probe unit, for movement through the interior portion of the structure together with the outer probe unit. The inner probe unit may comprise a first inner probe unit member and a second inner probe unit member at least one of the first inner probe unit member and second inner probe unit member magnetically coupled to at least one of the first outer probe unit member and the second outer probe unit member by magnetic attraction between a magnet on the respective one of the first and second inner probe unit members and the respective one of the first and second outer probe unit members, to maintain each of the respective one of the first and second inner probe unit members and the respective one of the first and second outer probe unit members in close proximity to a respective wall of the structure. The first inner probe unit member and second inner probe unit member may be forced apart through magnetic repulsion between a magnet on the first inner probe unit member and a magnet on the second inner probe unit member.

The apparatus may comprise a magnetic balance guide rod extending from the first outer probe unit member through the second outer probe unit member to the magnetic balance, directing the movement of the second outer probe unit member between the first outer probe unit member and the magnetic balance. The apparatus may comprise at least one of the first outer probe unit member and the second outer probe unit member carrying a nondestructive inspection instrument transducer.

The disclosure also provides a method of inspecting a structure having an interior opening portion defined by a plurality of walls having exterior and interior surfaces, comprising: providing an inspection apparatus outer probe unit having a plurality of outer probe unit walls each having a surface corresponding to a respective one of the plurality of exterior surfaces of a respective structure wall, the outer probe unit comprising a first outer probe member and a second outer probe member, magnetically coupled to each other to thereby force at least one outer probe unit wall on the first outer probe unit member and at least one outer probe unit wall on the second outer probe unit member into close proximity to a respective exterior surface of the structure, through magnetic attraction between a magnet on the first outer probe unit member and a magnet on the second outer probe unit member, and a magnetic balance positioned to force the second outer probe unit member in a direction of increased magnetic coupling of the second outer probe unit member to the first outer probe unit member through magnetic repulsion between a magnet on the magnetic balance and a magnet on the second outer probe unit member; providing an inspection apparatus inner probe unit having a plurality of inner probe unit walls each having a surface corresponding to a respective one of the interior surfaces of the structure; the inner probe unit being magnetically coupled through the structure to the outer probe unit by magnetic attraction of a magnet on the inner probe unit and a magnet on the outer probe unit, for movement through the interior portion of the structure together with the outer probe unit; and transmitting inspection signals into and receiving inspection signals from the structure as the probes are moved along the structure.

BRIEF DESCRIPTION OF THE DRAWINGS

The present disclosure will be described more fully with reference to the accompanying drawings. Some, but not all, embodiments of the invention are shown. The invention may be embodied in many different forms and should not be construed as limited to the described embodiments. The features, functions, and advantages that are disclosed can be achieved independently in various embodiments of the present disclosure or may be combined in yet other embodiments further details of which can be seen with reference to the following description and drawings, wherein like numerals and variable depict, respectively, like parts and parameters, and wherein.

DETAILED DESCRIPTION

The present disclosure provides for repulsive magnetic force balancing or cushioning of the attractive magnetic force coupling of the interior and exterior probe assemblies as the NDI apparatus moves along the structure being inspected, such as a hat stringer structural support.

Figure 1:
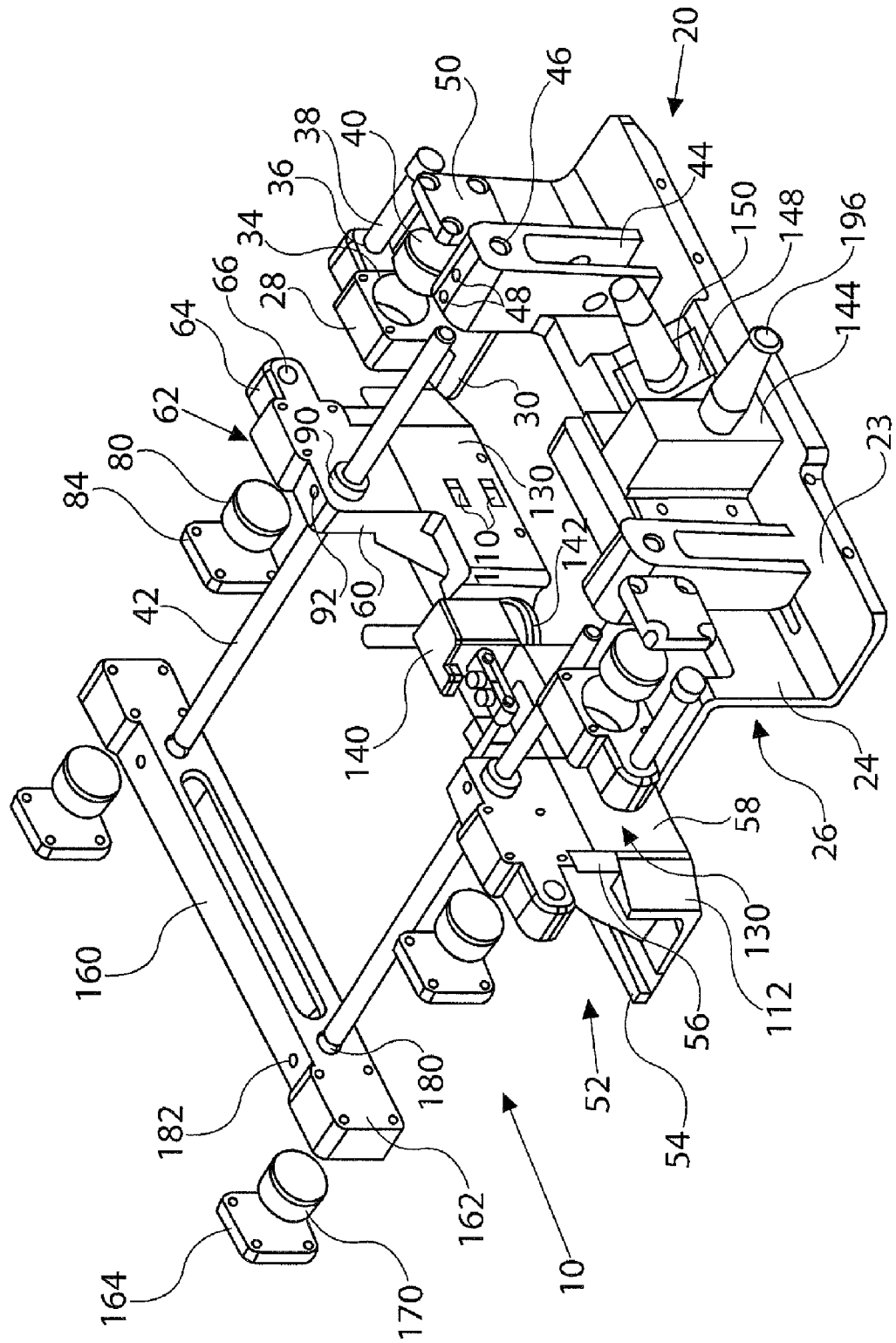
FIG. 1 shows an exploded perspective view of an exterior probe assembly portion of a nondestructive inspection apparatus according to aspects of an embodiment of the present disclosure.

Referring to FIG. 1 there is illustrated by way of example an exterior probe assembly portion 10 of a non destructive inspection ("NDI") system, which may be utilized along with a inspection system inner probe assembly 12 (shown in FIG. 2) to perform nondestructive inspection of structures having walls defining a length of enclosed space, such as a hat stringer structural support (hereinafter for convenience collectively "hat stringers").

The outer probe assembly 10 may have a probe fixture 20, having a probe fixture footing 23 and a probe fixture side wall 24. The side wall 24 may have an inner contact surface 26, on which may be mounted wheel bearings (not shown) to facilitate movement of the probe fixture along the hat stringer exterior side wall surface.

The probe fixture 20 may have a magnet housing 28 mounted on a magnet housing bracket arm 30. The magnet housing may have a gap control extension 34 through which may be formed a threaded gap control screw hole 36 in which to threadedly engage a gap control screw 38. The magnet housing 28 may house a magnet 40 held in place by a magnet housing cover 50.

An NDI system assembly shaft 42 may extend through a shaft through hole 46 in shaft mounting tower 44 portion of the side wall 24. The position of the probe fixture portion 20 on the shaft 42 may be fixed by a pair of shaft set screws 48.

The exterior/outer probe assembly 10 may also include an encoder member 52, which may have an encoder member footer 54 and an encoder member side wall 56, having an interior contact surface 58 on which may be mounted wheel bearings 110, some of which may be seen in FIG. 1.

Figure 2:
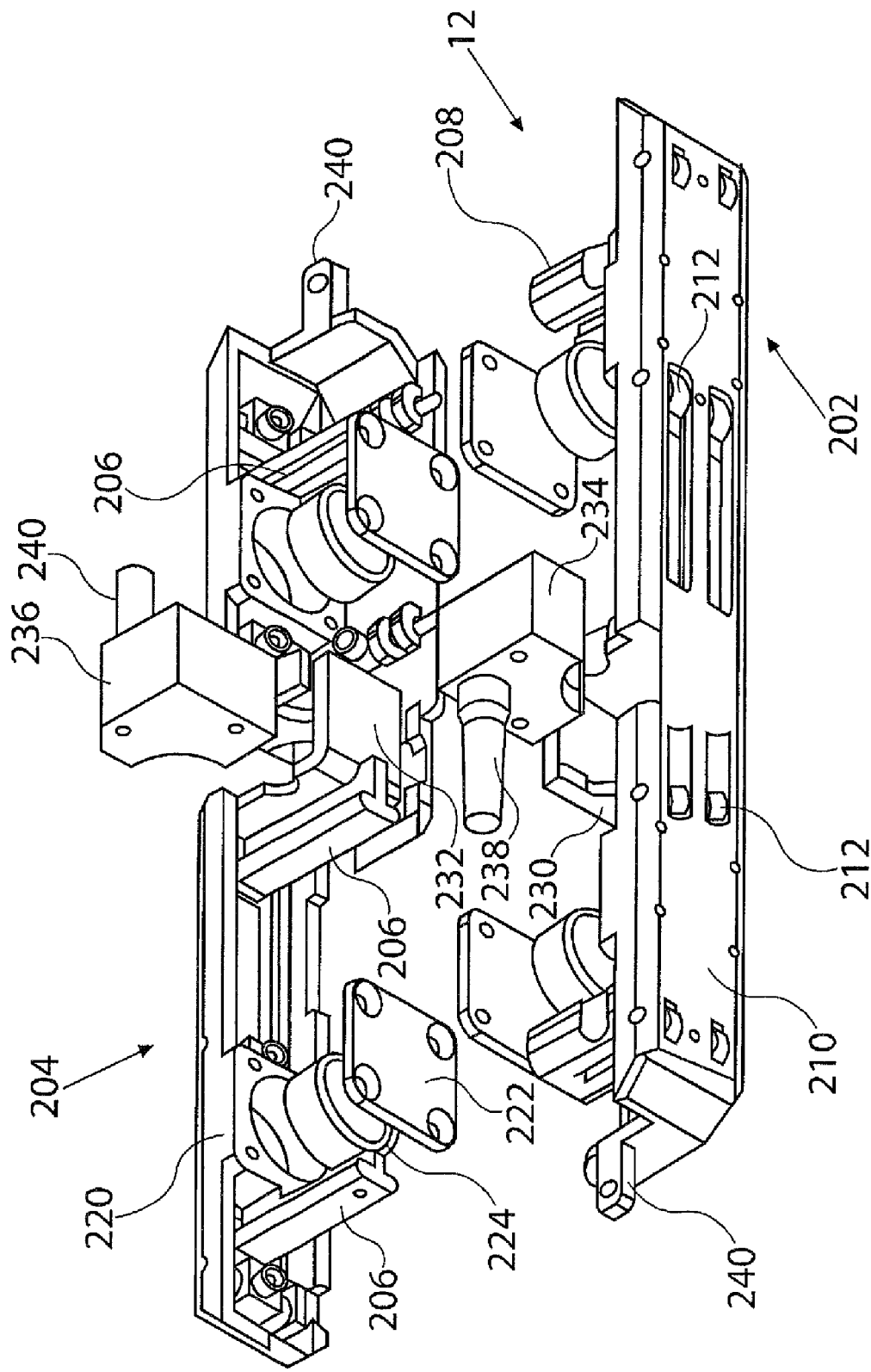
FIG. 2 shows an exploded perspective view of an interior probe assembly portion of a nondestructive inspection apparatus according to aspects of an embodiment of the present disclosure.

The encoder member side wall 56 may have a magnet housing bracket 60 which may contain a magnet housing 62. The magnet housing bracket 60 may also contain a gap control extension 64 in which may be formed a gap control screw abutment indentation 66. A magnet 80 may be housed in the magnet housing 62 held in place by a magnet housing cover 84. The magnet housing bracket 60 may also house a shaft linear bearing 90, which may be held in place in the magnet housing bracket 60 by a pair of bearing set screws 92. The encoder member 52 may have a tapered opening side wall inner contact surface 112. The encoder member may also have magnetic coupling magnets (not shown), as is well known in the art, in magnet housings in positions indicated by lead lines 130, lower down on the side wall 58 of the exterior probe assembly second member, encoder member 52, for magnetic coupling with the interior probe assembly 12 (FIG. 2).

It will be understood that the structures above described are essentially replicated at the opposite ends of the respective probe fixture 20 and encoder member 52.

The encoder member 52 carries an encoder assembly 140 including an encoder wheel 142, which engages the outer sidewall of a structure being inspected and measures position along the length of the structure. The probe fixture 20 carries one or more probe transducers, contained in such as transducer housing 144 for transducer 196 and transducer housing 148 for transducer 150.

The exterior probe assembly 10 also includes a magnetic balance apparatus, which balances/cushions the magnetic coupling of the exterior probe assembly 10 with the interior probe carrier, shuttle 12. The cushioning mechanism may include a shaft bar 160 with a pair of magnet housings 162 at respective ends of the shaft bar 160 containing magnets 170 held in place by a magnet housing cover 164. The shaft bar 160 has a pair of shaft openings 180 and is held in place on the shafts 42 by respective set screws 182.

Turning now to FIG. 2, there is illustrated by way of example an exploded perspective view of an interior probe assembly portion 12 of a nondestructive inspection apparatus according to aspects of an embodiment of the present disclosure. The interior probe unit assembly 12 may have a probe unit assembly first member, right side 202 and a probe unit assembly second member, left side 204. The sides 202, 204 are adjustable in position with respect to each other to adjust to a structure being inspected that varies in separation of its side walls, by slideably engaging respective ones of a plurality of separation adjustment slides 206 within respective separation adjustment slide receptors 208.

In this manner, the respective contact side wall 210 of the right side 202 and left side 204 can be maintained in close contact with the respective structure side wall, having wheel bearings 212 to facilitate movement along the structure wall. The right side 202 and left side 204 may be urged away from each other by the opposing magnetic force of magnets 224 contained in respective magnet housings 220 and held in place by a magnet housing cover 222.

The inner probe shuttle 12 may carry on each side a respective transducer 238, 240 held within a respective transducer compartment 230, 232, including a respective transducer housing 234 236.

Figure 5:
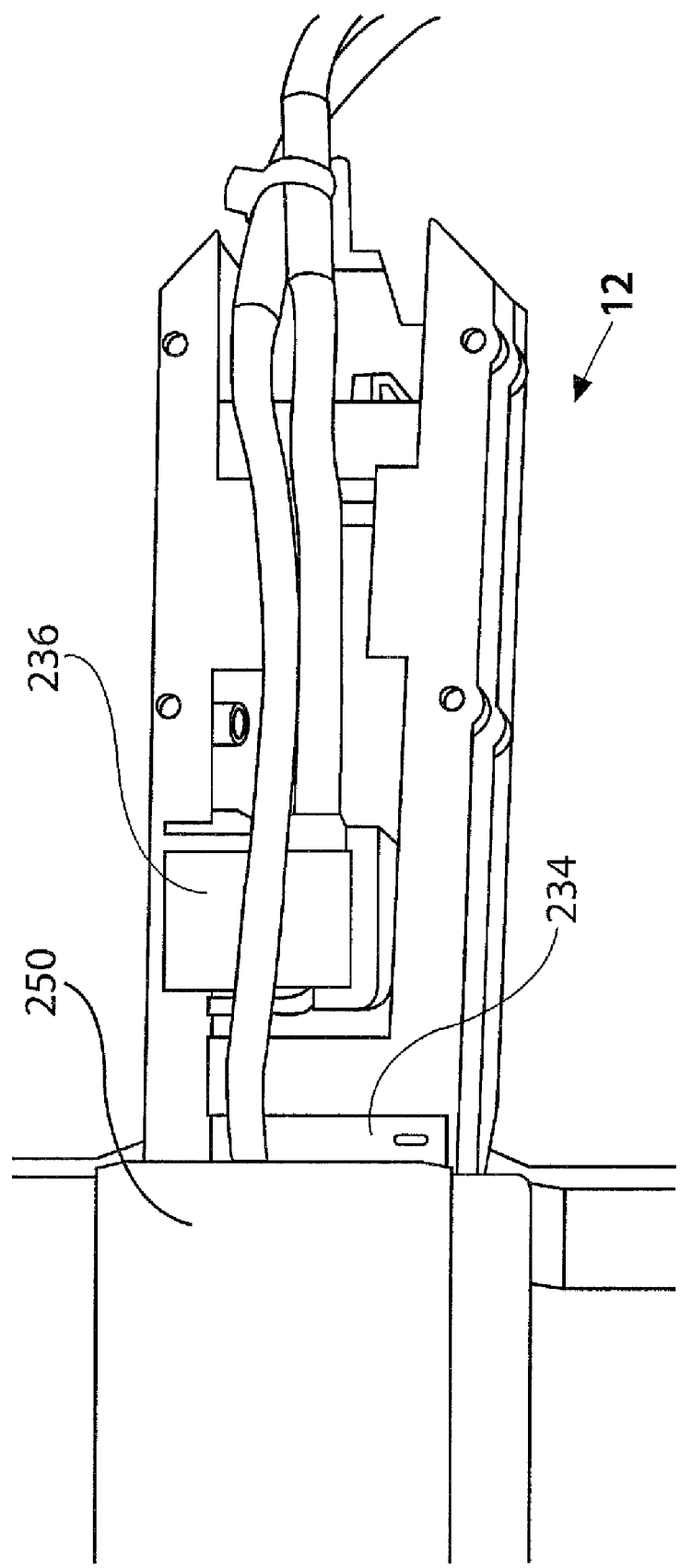
FIG. 5 shows the interior probe assembly partly inserted into the interior of a structure to be inspected.

FIG. 5 is a top view of the exterior probe assembly 10 as illustrated in FIG. 1.

Figure 3:
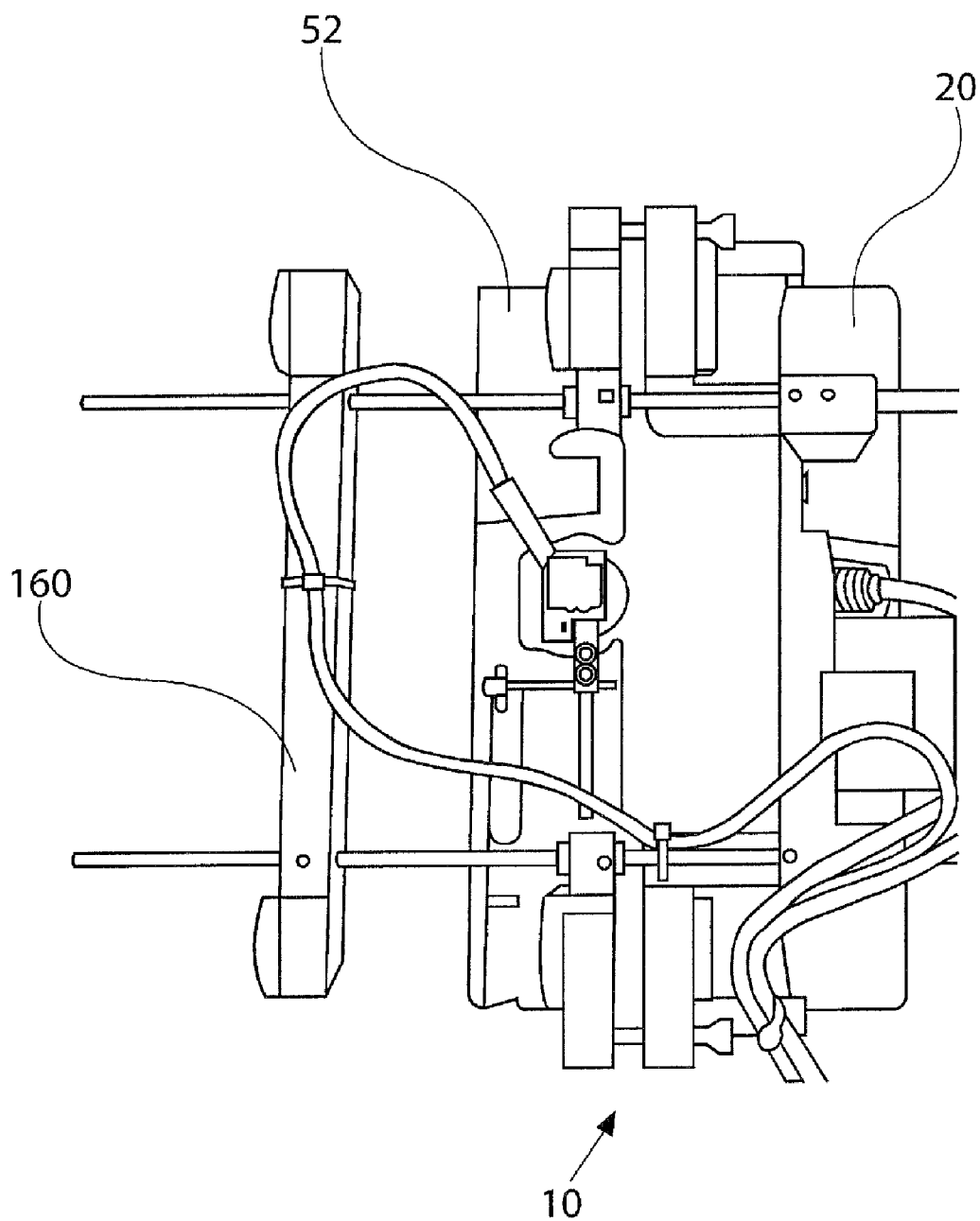
FIG. 3 shows a top view of the exterior probe assembly of FIG. 1.
Figure 4:
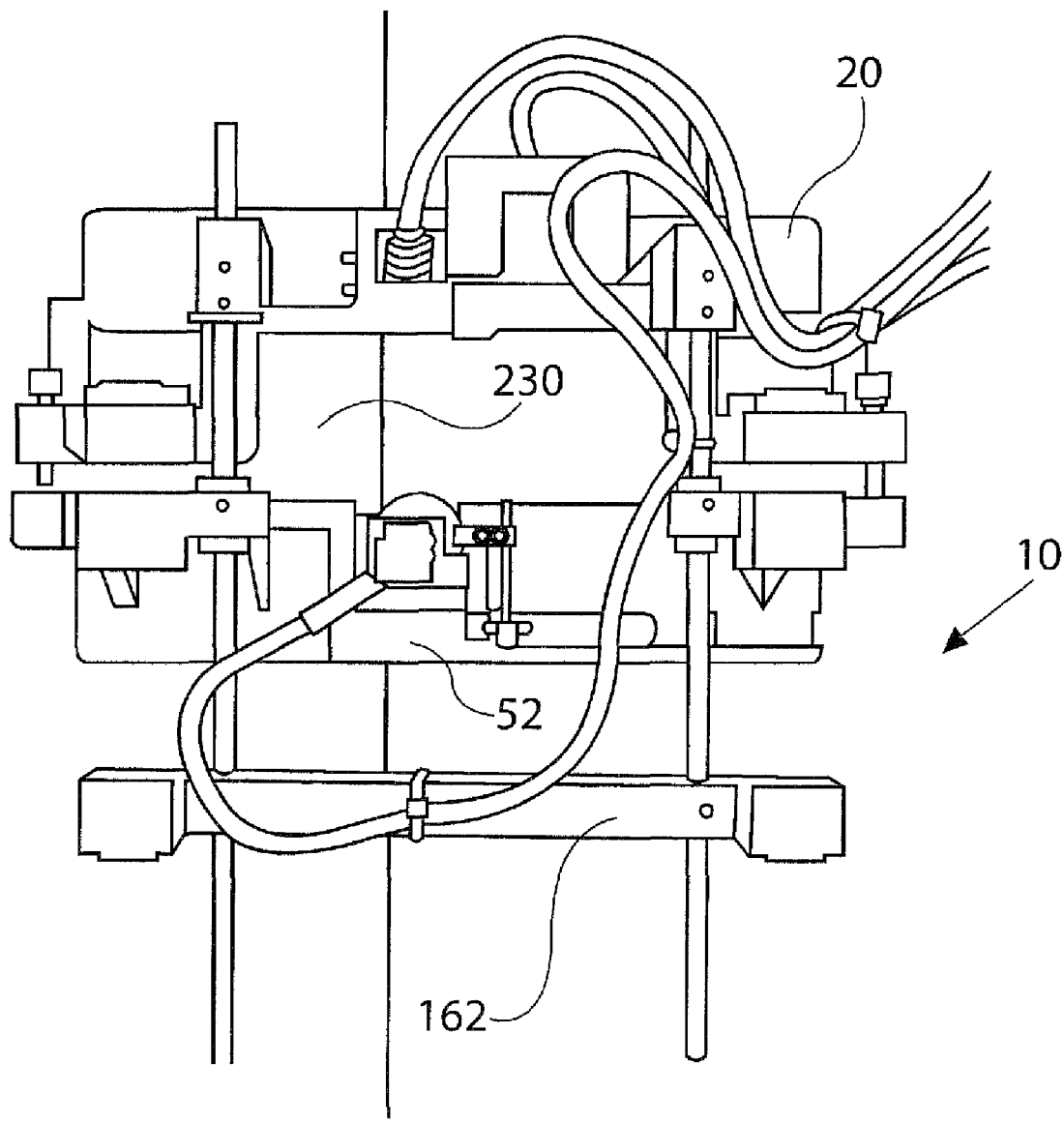
FIG. 4 shows the exterior probe assembly partially engaging the outer portions of a structure to be inspected.

In operation, it will be understood, the interior probe 12 is inserted into an opening in a structure 250, such as a hat stringer, as illustrated in FIG. 5. The exterior probe assembly shown in the top view of FIG. 3 is then placed on the outside of the structure 250, as illustrated in FIG. 4. Magnetic coupling occurs between the magnets 224 of the inner probe shuttle 12 and the magnets contained in the magnet housings 130, as illustrated to be in the encoder member sidewall 56. It will be understood that only magnet housings 130 on the encoder member sidewall 56, a possible embodiment for the exterior assembly 10, while magnetic coupling magnets 224 have been illustrated on both sides of the inner probe 12, also a possible embodiment, in which event the exterior assembly 10 could also be constructed to contain magnetic coupling magnets for magnetic coupling to the inner probe shuttle 12 on one side, as illustrated in FIG. 1 or on both sides. The gap control screw may be adjusted to set a minimum separation between the probe fixture 20 and the encoder assembly 52 of the exterior probe assembly 10.

In operation the inner probe 12 will be dragged along with the exterior probe assembly 10 as the exterior probe assembly moves along the structure 250, as is well known in the art, due to the attractive force of the magnetic interior/exterior probe magnetic coupling magnets. The right side 202 and left side 204 of the inner probe 12 can move with respect to each other to maintain the wheel bearings 212 on the sides 202, 204 in contact with a respective inner side wall of the structure 250, due to magnetic attractive forces between the magnets 224 on the sides 202, 204 of the inner probe 12 and the magnets (not shown) in the magnet housings 130 of the outer assembly (illustrated by way of example here to be only in the encoder assembly 52 of the exterior probe assembly 10.

The probe fixture 20 and encoder assembly 52 of the exterior probe assembly 10 are maintained in close contact with the respective exterior side wall of the structure 250 by the attractive forces of the magnets 40, 80 in the magnetic housings 28,62 on the magnetic housing brackets 30 and 60 in the side walls 24, 52 of the probe fixture 20 and encoder assembly 52. The magnets 170 on the shaft bar 162 are positioned to be in repulsing force with the magnets 80 on the encoder assembly 52. Thus, in addition to the inter/exterior attractive magnetic coupling there is an additional magnetic force pushing the encoder assembly 52 toward the respective side wall of the structure 250. The encoder assembly, under the combined influence of the attractive magnetic coupling between the probe fixture magnets 40 and the encoder assembly magnets 80 and the repulsive magnetic force between the encoder assembly magnets 80 and the shaft bar magnets 170, moves on the shafts 42 through the shaft bearings 90 to adjust to the changes in width of the structure 250 being inspected, and also to the variations in surface texture or other surface irregularities of the structure 250 side walls. This greatly reduces the chances of the interior/exterior magnetic coupling being lost.

The scope and content of the present disclosure are not limited to the above embodiments but should be considered in scope and content taking into account the manner in which the disclosed embodiments may be changed and modified without departing from the scope and spirit of the disclosed subject matter and claims, some of which changes and modifications have been noted above.

What is claimed is:

1. A nondestructive inspection apparatus adapted to inspect a structure having an interior opening portion defined by a plurality of walls having exterior and interior surfaces, comprising:
    an inspection apparatus outer probe unit having a plurality of outer probe unit walls each having a surface corresponding to a respective one of the plurality of exterior surfaces of a respective structure wall, the outer probe unit comprising a first outer probe member and a second outer probe member, magnetically coupled to each other to thereby force at least one outer probe unit wall on the first outer probe unit member and at least one outer probe unit wall on the second outer probe unit member into close proximity to a respective exterior surface of the structure, through magnetic attraction between a magnet on the first outer probe unit member and a magnet on the second outer probe unit member; and
    a magnetic balance positioned to force the second outer probe unit member in a direction of increased magnetic coupling of the second outer probe unit member to the first outer probe unit member through magnetic repulsion between a magnet on the magnetic balance and a magnet on the second outer probe unit member.

2. The nondestructive inspection apparatus of claim 1, further comprising:
    an inspection apparatus inner probe unit having a plurality of inner probe unit walls each having a surface corresponding to a respective one of the interior surfaces of the structure;
    the inner probe unit being magnetically coupled through the structure to the outer probe unit by magnetic attraction of a magnet on the inner probe unit and a magnet on the outer probe unit, for movement through the interior portion of the structure together with the outer probe unit.

3. The nondestructive inspection apparatus of claim 2, wherein at least one of the first outer probe unit member and the second outer probe unit member and the inner probe unit carries a nondestructive inspection instrument.

4. The nondestructive inspection apparatus of claim 2, wherein the inner probe unit comprises a first inner probe unit member and a second inner probe unit member at least one of the first inner probe unit member and second inner probe unit member magnetically coupled to at least one of the first outer probe unit member and the second outer probe unit member by magnetic attraction between a magnet on the at least one of the first and second inner probe unit members and the at least one of the first and second outer probe unit members, to maintain each of the at least one of the first and second inner probe unit members and the at least one of the first and second outer probe unit members in close proximity to a wall of the structure.

5. The nondestructive inspection apparatus of claim 4, wherein the first inner probe unit member and the second inner probe unit member are forced apart through magnetic repulsion between a magnet on the first inner probe unit member and a magnet on the second inner probe unit member.

6. The nondestructive inspection apparatus of claim 4, wherein at least one of the first outer probe unit member and second outer probe unit member and the first inner probe unit member and the second inner probe unit member carries a nondestructive inspection instrument transducer.

7. The nondestructive inspection apparatus of claim 1, wherein a magnetic balance guide rod extends from the first outer probe unit member through the second outer probe unit member to the magnetic balance, directing movement of the second outer probe unit member between the first outer probe unit member and the magnetic balance.

8. The nondestructive inspection apparatus of claim 1, wherein at least one of the first outer probe unit member and the second outer probe unit member carries a nondestructive inspection instrument transducer.

9. A method of inspecting a structure having an interior opening portion defined by a plurality of walls having exterior and interior surfaces, comprising:

providing an inspection apparatus outer probe unit having a plurality of outer probe unit walls each having a surface corresponding to a respective one of the plurality of exterior surfaces of a respective structure wall, the outer probe unit comprising a first outer probe member and a second outer probe member, magnetically coupled to each other to thereby force at least one outer probe unit wall on the first outer probe unit member and at least one outer probe unit wall on the second outer probe unit member into close proximity to a respective exterior surface of the structure, through magnetic attraction between a magnet on the first outer probe unit member and a magnet on the second outer probe unit member, and a magnetic balance positioned to force the second outer probe unit member in a direction of increased magnetic coupling of the second outer probe unit member to the first outer probe unit member through magnetic repulsion between a magnet on the magnetic balance and a magnet on the second outer probe unit member;

providing an inspection apparatus inner probe unit having a plurality of inner probe unit walls each having a surface corresponding to a respective one of the interior surfaces of the structure; the inner probe unit being magnetically coupled through the structure to the outer probe unit by magnetic attraction of a magnet on the inner probe unit and a magnet on the outer probe unit, for movement through the interior portion of the structure together with the outer probe unit; and transmitting inspection signals into and receiving inspection signals from the structure as the probes are moved along the structure.

10. The method of claim 9, wherein the inner probe unit comprises a first inner probe unit member and a second inner probe unit member at least one of the first inner probe unit member and second inner probe unit member magnetically coupled to at least one of the first outer probe unit member and the second outer probe unit member by magnetic attraction between a magnet on the at least one of the first and second inner probe unit members and the at least one of the first and second outer probe unit members, to maintain each of the at least one of the first and second inner probe unit members and the at least one of the first and second outer probe unit members in close proximity to a wall of the structure.

11. The method of claim 10, wherein at least one of the first outer probe unit member and the second outer probe unit member and the inner probe unit carries a nondestructive inspection instrument.

12. The method of claim 10, wherein the first inner probe unit member and the second inner probe unit member are forced apart through magnetic repulsion between a magnet on the first inner probe unit member and a magnet on the second inner probe unit member.

13. The method of claim 9, wherein a magnetic balance guide rod extends from the first outer probe unit member through the second outer probe unit member to the magnetic balance, directing movement of the second outer probe unit member between the first outer probe unit member and the magnetic balance.

14. The method of claim 13, wherein at least one of the first outer probe unit member and second outer probe unit member and the first inner probe unit member and the second inner probe unit member carries a nondestructive inspection instrument transducer.

15. The method of claim 9, wherein at least one of the first outer probe unit member and the second outer probe unit member carries a nondestructive inspection instrument transducer.

* * * * *